United States Patent
Gumbrecht et al.

(10) Patent No.: US 7,510,839 B2
(45) Date of Patent: Mar. 31, 2009

(54) METHOD FOR THE COMBINED ISOLATION OF MAGNET-BEADS FROM A LIQUID SAMPLE AND SUBSEQUENT THERMOCYCLISATION FOR THE POLYMERASE CHAIN REACTION (PCR) AND ASSOCIATED ARRANGEMENT

(75) Inventors: Walter Gumbrecht, Herzogenaurach (DE); Peter Paulicka, Erlangen (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/665,376

(22) PCT Filed: Oct. 14, 2005

(86) PCT No.: PCT/EP2005/055272

§ 371 (c)(1),
(2), (4) Date: Apr. 13, 2007

(87) PCT Pub. No.: WO2006/042826

PCT Pub. Date: Apr. 27, 2006

(65) Prior Publication Data
US 2007/0264649 A1    Nov. 15, 2007

(30) Foreign Application Priority Data
Oct. 15, 2004    (DE) .................. 10 2004 050 575

(51) Int. Cl.
*C12Q 1/68*    (2006.01)
*G01N 33/557*    (2006.01)
*G01N 33/553*    (2006.01)
*G01N 33/536*    (2006.01)
*C12P 19/34*    (2006.01)

(52) U.S. Cl. .................. 435/6; 435/91.1; 435/91.2; 436/517; 436/526; 436/536

(58) Field of Classification Search .............. 435/6, 435/91.1, 91.2; 436/517, 526, 536
See application file for complete search history.

(56) References Cited

U.S. PATENT DOCUMENTS

2004/0018611 A1 * 1/2004 Ward et al. ............ 435/287.2

FOREIGN PATENT DOCUMENTS

| WO | WO 2005105284 A1 | 11/2005 |
| WO | WO 2005106024 A1 | 11/2005 |

OTHER PUBLICATIONS

European Search Report, Jan. 14, 2008.
Waters L.C. et al.: "Multiple Sample PCR Amplification and Electrophoretic Analysis on a Microchip", Analytical Chemistry, American Chemical Soc., Bd. 70, Nr. 24, 15.12.98, S. 5172-5176.
Logally E. T. et al.: "Fully Integrated PCR-Capillary Electrophoresis Microsystem for DNA Analysis", LAB on a Chip, Royal Soc. of Chemistry, Cambridge, GB, Bd. 1, Nr. 2, Dez. 2001, S. 102-107.

(Continued)

*Primary Examiner*—Jezia Riley
(74) *Attorney, Agent, or Firm*—Harness, Dickey & Pierce, P.L.C.

(57) ABSTRACT

Embodiments generally relate to a PCR wherein a magnetic field is focused in a localized area and also to the possibility of a cyclic transfer of heat. According to at least one embodiment of the invention, a magnetic field gradient is constructed along the direction of flow and the transfer of heat is carried out in a manner perpendicular to the direction of flow. Suitable things are provided therefore. The magnetic field is, in particular, focused by Mumetal® which is arranged on both sides of the flow channel and the temperature is controlled by way of Peltier elements, cooling bodies, and thermal coupling plates.

16 Claims, 4 Drawing Sheets

OTHER PUBLICATIONS

Fellmann F. et al.: "Simplified Protocol of Solid-Phase CDNA Libraries for Multiple PCR Amplification", Biotechniques, Informa Life Sciences Publishing, Westborough, MA, US, Bd. 21, Nr. 5, Nov. 1996, S. 766, 768, 770.

Choi Jin-Woo et al.: "An integrated microfluidic biochemical detection system for protein analysis with magnetic bead-based sampling capabilities", LAB on a Chip, Feb. 2002, Bd. 2, Nr. 1, Feb. 2002, S. 27-30.

* cited by examiner

METHOD FOR THE COMBINED ISOLATION OF MAGNET-BEADS FROM A LIQUID SAMPLE AND SUBSEQUENT THERMOCYCLISATION FOR THE POLYMERASE CHAIN REACTION (PCR) AND ASSOCIATED ARRANGEMENT

PRIORITY STATEMENT

This application is the national phase under 35 U.S.C. § 371 of PCT International Application No. PCT/EP2005/055272 which has an International filing date of Oct. 14, 2005, which designated the United States of America and which claims priority on German Patent Application number 10 2004 050 575.6 filed Oct. 15, 2004, the entire contents of which are hereby incorporated herein by reference.

FIELD

Embodiments of the invention generally relate to a method for the combined isolation of magnetic beads from a liquid sample and subsequent thermocycling with the polymerase chain reaction (PCR). In addition, embodiments of the invention also generally relate to the associated arrangement for carrying out the method.

BACKGROUND

For the nucleic acid analysis of, for example, white blood cells from whole blood to answer questions concerning such matters as the human genome, cells must first be broken open in a sample preparation step and the DNA freed in this way must subsequently be isolated. At the same time, constituents of the blood such as for example hemoglobin, immunoglobulins and lactoferrin, which could inhibit a subsequent polymerase chain reaction, must be removed.

These working steps are carried out in a laboratory on the basis of the known prior art. So, apart from other procedures, cells may be broken open with alkaline solution (NaOH) and the DNA subsequently bonded to silica-coated magnetic beads. By applying a magnetic field, the magnetic beads charged with DNA can be securely held and washed. The isolated DNA can subsequently be eluted from the beads or used together with the beads (as a DNA/bead complex) for the PCR.

In DE 10 2004 021822 A1, which is not a prior publication, it is described how magnetic isolation and a polymerase chain reaction are combined in an integrated miniaturized cartridge. In this case, attention is mainly given to the arrangements in the cartridge. It is not disclosed there how the controlling and actuating device must be constructed in order to realize combined microfluidics, bead isolation and thermocycling.

SUMMARY

At least one embodiment of the invention is directed to a method for the combined isolation of the magnetic beads with suitable possibilities for thermocycling. In addition, an associated arrangement is to be provided.

Both magnetic bead isolation by way of a magnetic field gradient and thermocycling with, for example, Peltier elements are known per se. However, at least one embodiment of the invention for the first time succeeds in allowing a combination of the two operations to take place in an extremely confined space. The method/device for rapid heat transfer and the method/device for application of a strong magnetic field gradient are realized at the same place, so that both measures can take place simultaneously, in particular in a space of approximately 10 mm$^3$.

With at least one embodiment of the invention it is possible in an advantageous way to prescribe magnetic fields or field gradients that lead to the desired concentration of the magnetic beads in an extremely confined space. However, it is also possible, by suitable polarization, to generate divergent fields which influence the magnetic beads. Timed switching-over of the polarity allows a particularly good mixture of substances intended for the PCR, which are bonded to the magnetic beads, to be achieved, in particular by magnetic "stirring".

BRIEF DESCRIPTION OF THE DRAWINGS

Further details and advantages of the invention emerge from the following description of figures of example embodiments on the basis of the drawing in conjunction with the patent claims. In the drawings:

DETAILED DESCRIPTION OF THE EXAMPLE EMBODIMENTS

Figure 1:
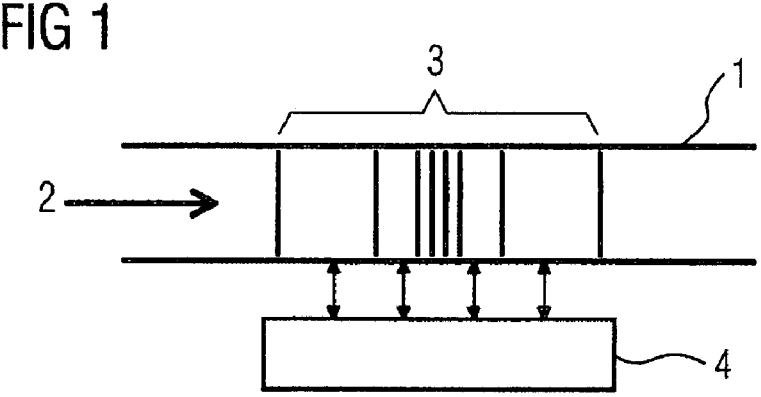
FIG. 1 shows the principle of an embodiment of the invention in a roughly schematic representation.

In FIG. 1, a flow channel 1 in which a liquid flow 2 is realized in the direction of the arrow is represented. A magnetic field gradient 3 is built up along the direction of flow, for which purpose field lines extend from a source with differing densities. Perpendicular to the direction of flow, a heat transfer is realized, for which purpose there is a unit 4.

In order to ensure rapid heat transfer for the thermocycling in the PCR, the PCR chamber is kept as small as possible in one geometrical dimension (about 1 mm or volume<20 μl) and the heat transmissions are realized in a "sandwich" thermostating arrangement such that only small films of liquid (a few 100 μm) have to be brought into thermal equilibrium. The PCR chamber is preferably located in a housing with plane-parallel outer surfaces (polymer sheet with clearance and film closure). The inflow and outflow of the PCR chamber run parallel to the polymer sheet or closure film. Peltier elements, which are pressed against the plane-parallel outer surfaces of the PCR chamber via thin plates with good thermal conductivity (for example aluminum) are used as thermal actuators. The respective opposite sides of the Peltier elements are made to contact bodies (coolers) which make it possible for heat to be transmitted to the ambient air over a surface that is as large as possible, possibly with the assistance of fans.

PCR heating plates arranged in such a way do not allow any further direct combination with a strong magnetic field (for example a permanent magnet, electromagnet) for isolation of the magnetic beads in the middle of the construction.

A PCR chamber arranged in such a way, which is enclosed by relatively voluminous components, cannot be combined directly with an electromagnet or permanent magnet for the isolation of the magnetic beads.

In order nevertheless to achieve a high field gradient in the PCR chamber along the direction of flow of the liquid containing the magnetic beads, the thermally conductive but magnetically neutral plates for the heat transmission from the Peltier elements to the PCR chamber will provide the PCR housing with small-volume bodies (about 5 mm$^3$) of a material with a high relative permeability $\mu(r)$ and at the same time still good thermal conductivity, preferably permalloy (Ni—Fe) or mu-metal (Ni/Fe/Cu/Mo).

These small-volume bodies respectively form a magnetic core directly on the surfaces of the PCR chamber and are incorporated in the heating plates. The PCR chamber is then located directly between the magnetic cores. Such magnetic cores can be magnetized with an externally applied magnetic field. According to at least one embodiment of the invention, for example, permanent magnets are located on the outer sides of Peltier elements, the magnetic field lines of which are concentrated by means of the magnetic cores and consequently generate a high field gradient.

In the field gradient, which is arranged parallel to the outer walls of the PCR chamber and the direction of flow of the solution containing magnetic beads, the magnetic beads are drawn in, securely held and consequently concentrated.

In combination with a "large-volume magnetic field", which is arranged perpendicular to the parallel outer walls of the PCR chamber, a great field gradient can be achieved within the PCR chamber along the direction of flow of the solution containing the magnetic beads, in that the "large-volume" field lines are concentrated with the aid of the mu-metal bodies in the PCR chamber.

Figure 2:
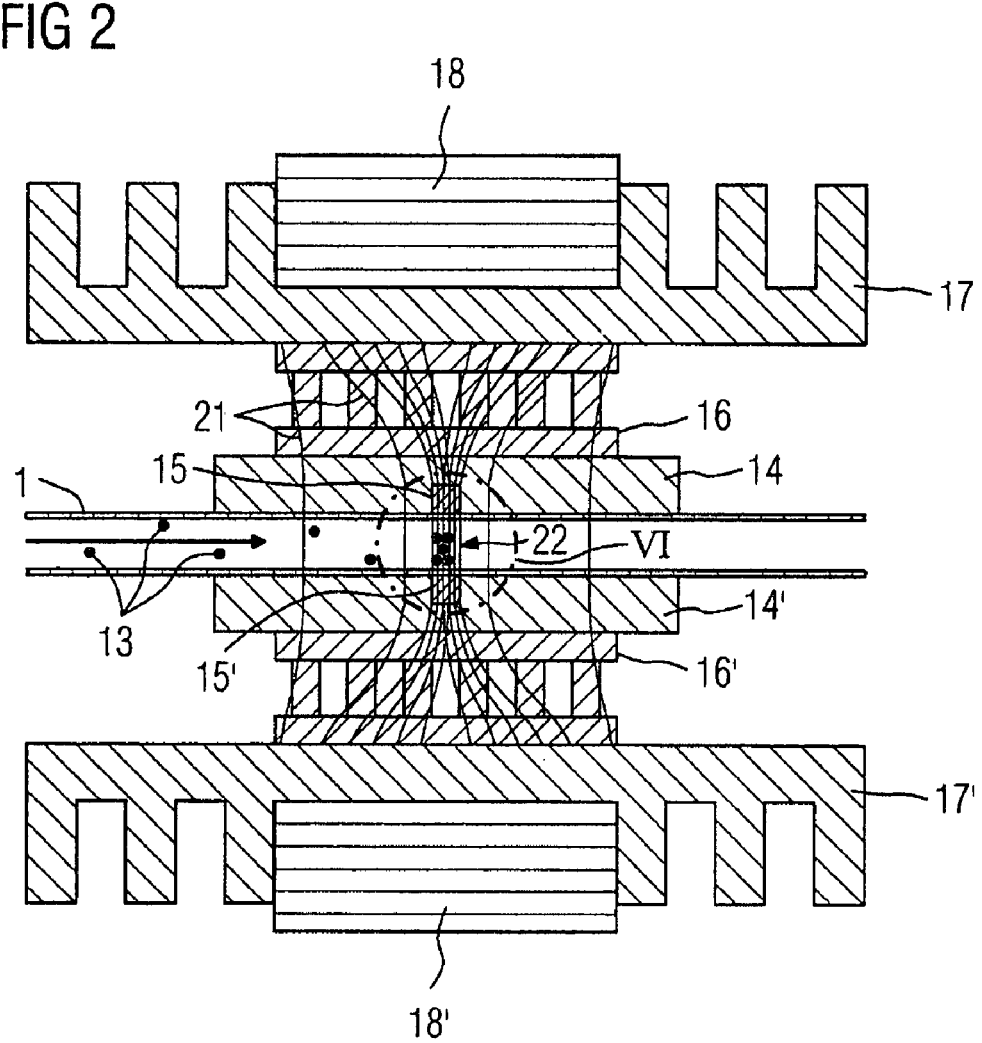
FIG. 2 shows an actual arrangement in section, with a device/method for concentrating magnetic beads in a highly localized place and with device/method for heat transfer.

In FIG. 2, the actual devices for realizing the method that is schematically represented in FIG. 1 are indicated. Once again, 1 denotes a flow channel with a liquid flow 2. In the liquid there are individual magnetic beads for coupling to DNA, which are denoted by 13. The magnetic beads 13 are to be concentrated in a highly localized area of the sample chamber.

The arrangement according to FIG. 2 substantially includes units arranged in layers on both sides of the flow channel, which on the one hand permit the focusing of the magnetic field and on the other hand permit the heat transmission: 14, 14' designate two heat coupling plates, let into which there is a respective mu-metal body 15, 15', lying opposite each other and centrally. Over the heat coupling plates 14, 14' there are devices 16, 16' with Peltier elements 17, 17' and over the latter there are permanent magnets 18, 18'. Instead of the permanent magnets, electromagnets may also be used.

The magnetic field pattern is also detected in FIG. 2. It is evident that a field pattern that is concentrated in the mu-metal bodies 15, 15' is realized on the basis of permanent magnets 18, 18' arranged with the same polarity. In a corresponding way, the magnetic beads 13 are concentrated in this area.

With the device represented, it is therefore possible in a surprisingly simple way on the one hand to generate a concentrated magnetic field at a localized place by a comparatively remote magnetic field generator and on the other hand correspondingly to subject this place with the surrounding areas to thermostatic control or thermocycling, as is necessary in particular for carrying out a PCR. The combination of Peltier elements and respectively associated cooling body serves in particular for the latter purpose.

Figure 3:
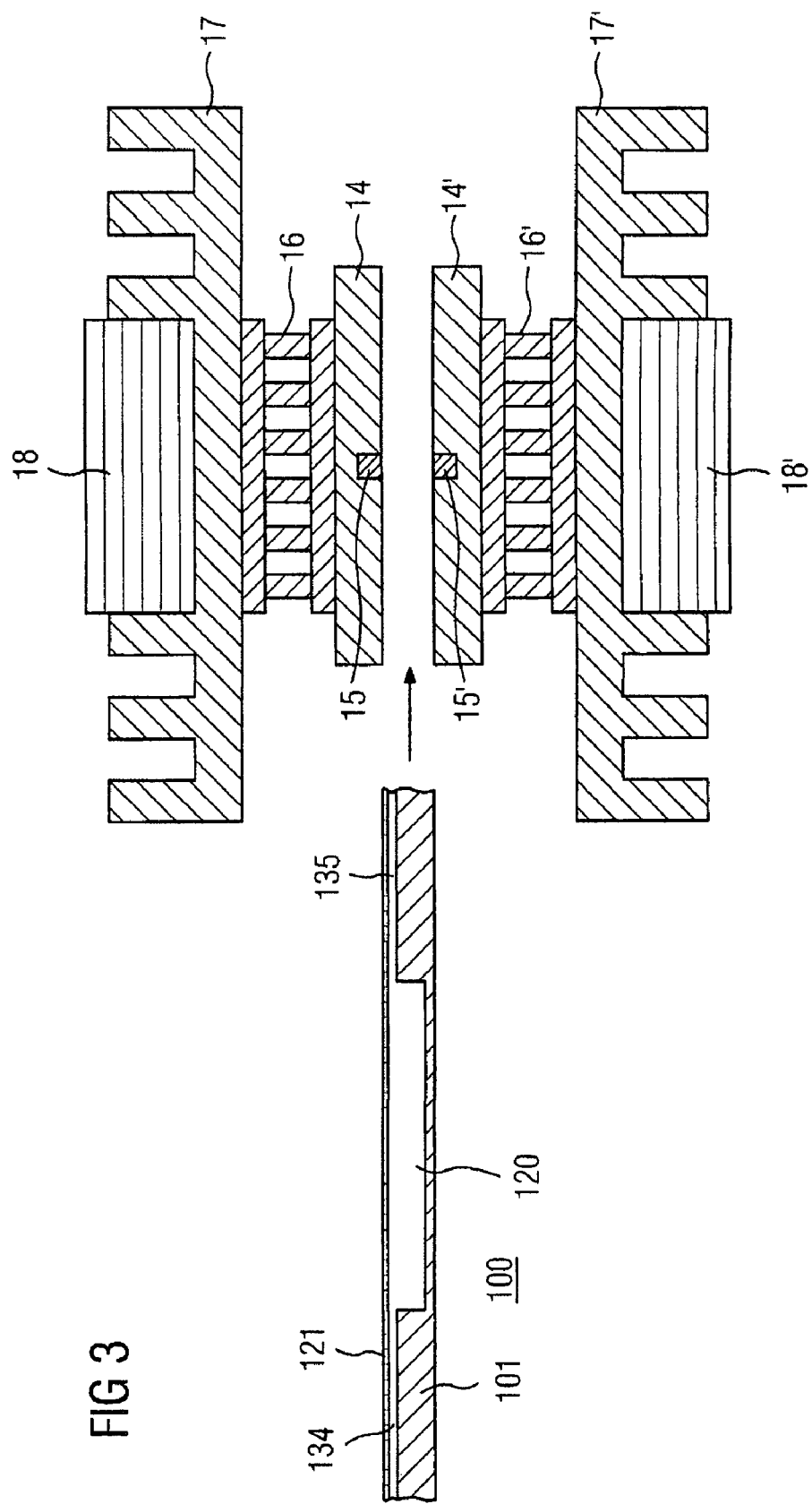
FIG. 3 shows such an arrangement with a cartridge which can be pushed into it.

In FIG. 3, the arrangement according to FIG. 2 is represented with a free space in which there is initially no cartridge. Indicated outside the arrangement is a cartridge 100, which can be pushed into the free space of the arrangement according to FIG. 3 and in which the desired measures can be carried out. The cartridge 100 in this case includes a planar plastic body 101 and an adhesive film 121 as a covering. This arrangement forms a sample chamber 120, which has an inflow 134 and an outflow 135.

Figure 4:
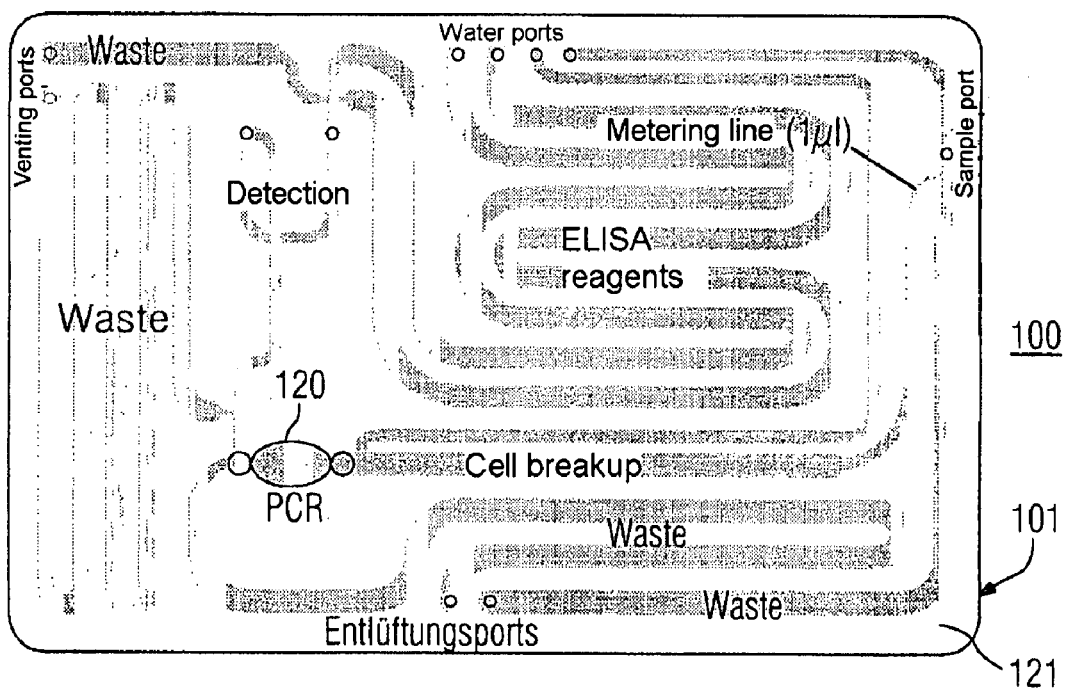
FIG. 4 shows the cartridge in plan view.

FIG. 4 shows the plan view of a cartridge 100 such as that essentially described in the application mentioned at the beginning. When the cartridge 100 is pushed into the free space of the arrangement according to FIG. 3, the PCR chamber 120, i.e. the sample chamber, is localized between the heat coupling plates 14, 14' with the mu-metal bodies 15, 15'.

In one particular embodiment of the invention, the PCR chamber (sample chamber) is closed during the thermocycling operation, for example in the inflow and outflow channel by valves 22, 22'. The valves 22, 22' supply constant pressure, pressing in particular against the film of the cartridge. To realize such valves, the properties of memory metals, as are described in an application by the applicant with the same priority, may be used for example.

Figure 5:
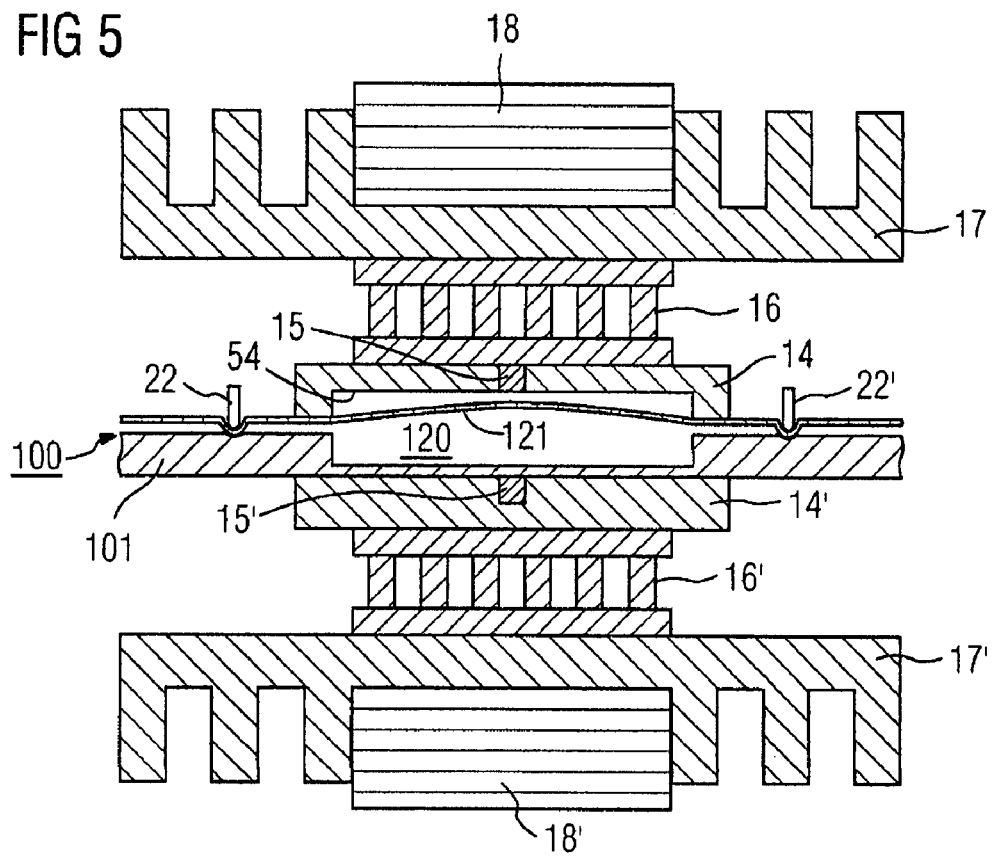
FIG. 5 shows a variant of the arrangement according to FIG. 3 with the cartridge pushed in and a device/method for pressure equalization.

On account of the great changes in temperature during the thermocycling, the pressure in the PCR chamber may rise as a result of air released by outgassing and the thermal expansion of the water. In FIG. 5, the arrangement according to FIG. 3 is modified to the extent that the upper heat coupling plate 14 of FIG. 2 has a clearance 54. The clearance 54 helps to provide the possibility that the covering film 32 can bulge into the clearance 54 and that a pressure equalization can consequently take place.

Figure 6:
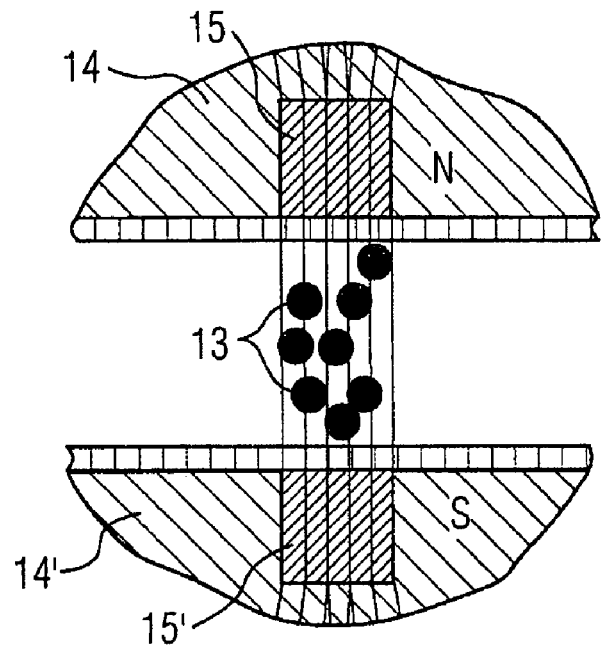
FIG. 6 shows a detail from FIG. 2.
Figure 7:
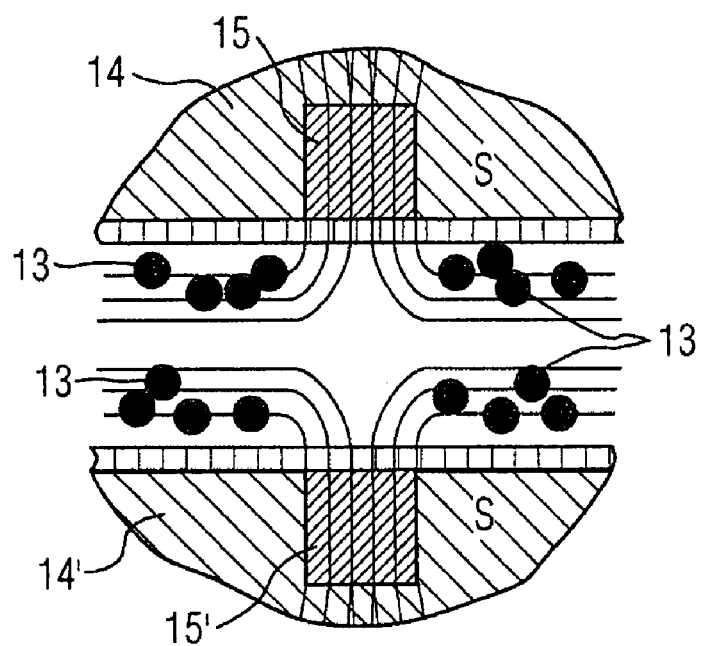
FIG. 7 shows the representation according to FIG. 6 with a different magnetic field configuration.

In FIG. 6 and FIG. 7, the area between the mu-metal elements 15, 15' is respectively represented as a detail taken from FIG. 2. In the first partial figure, it is shown that the magnetic flux is concentrated by the elements 15, 15', and the magnetic field lines extend approximately parallel in the channel 1. The magnetic beads 13, including DNA fragments bonded to them, are concentrated in this area, in order to carry out the PCR.

In the other partial figure, the magnetic poles of the upper magnets (not represented in detail) are reversed. This produces a divergent field pattern, with a field-free space in the middle between the elements 15, 15'. The magnetic beads 13 are correspondingly moved outward to the edges.

By switching over the magnetic poles in the upper area, a magnetic field that changes over time, alternating with the states according to FIG. 6 or FIG. 7, can therefore be generated in the upper area. This serves for mixing the sample liquid in the PCR chamber. An active stirring effect is obtained by the moving magnetic beads with the sample liquid bonded to them, which is advantageous for the PCR.

The switching-over of the magnetic poles may be achieved either by mechanical turning of permanent magnets or by use of correspondingly controllable electromagnets.

Example embodiments being thus described, it will be obvious that the same may be varied in many ways. Such variations are not to be regarded as a departure from the spirit and scope of the present invention, and all such modifications as would be obvious to one skilled in the art are

The invention claimed is:

1. A method for the isolation of magnetic beads from a liquid sample and subsequent thermocycling for a PCR (polymerase chain reaction), in which the liquid sample can flow in a flow channel to the sample chamber and the magnetic beads are isolatable there by a magnetic field with a field gradient in the direction of flow and subjected in the sample chamber to thermocycling, the method comprising:

building up the magnetic field gradient along the direction of flow; and realizing a heat transfer perpendicular to the direction of flow.

2. The method as claimed in claim 1, wherein the magnetic field is focused in a highly localized area of the sample chamber.

3. The method as claimed in claim 1, wherein the heat transfer takes place in the area of the sample chamber.

4. The method as claimed in claim 1, wherein the heat transmission perpendicular to the direction of flow is realized by a "sandwich" thermostating arrangement with heating/cooling elements.

5. An arrangement for the isolation of magnetic beads from a liquid sample and subsequent thermocycling for a PCR (polymerase chain reaction), in which the liquid sample can flow in a flow channel opening out to a sample chamber and the magnetic beads are isolatable there by a magnetic field with a field gradient in the direction of flow and subjectable in the sample chamber to thermocycling, the arrangement comprising:

means for generating a magnetic field gradient in the sample chamber along the direction of flow; and means for permitting thermostatic control of the sample chamber perpendicular to the direction of flow.

6. The arrangement as claimed in claim 5, wherein the means for generating the magnetic field includes at least one of a permanent magnet and an electromagnet, the magnetic field of which is feedable into the sample chamber by small-volume bodies of a material with high relative permeability and at the same time good thermal conductivity.

7. The arrangement as claimed in claim 6, wherein the material with high relative permeability is a permalloy (Ni—Fe) metal.

8. The arrangement as claimed in claim 6, wherein the material with high relative permeability is mu-metal (Ni/Fe/Cu/Mo).

9. The arrangement as claimed in claim 6, wherein the small-volume bodies of material with high relative permeability are incorporated in heating/cooling plates on both sides of the sample chamber.

10. The arrangement as claimed in claim 5, wherein heat coupling plates and heating/cooling elements are arranged in layers on both sides of the sample chamber for the thermocycling.

11. The arrangement as claimed in claim 10, wherein the heating/cooling elements are Peltier elements.

12. The arrangement as claimed in claim 11, wherein, apart from the Peltier elements, there are further devices for the thermal equalization of the Peltier elements with the surroundings.

13. The arrangement as claimed in claim 12, wherein the further devices are cooling ribs.

14. The arrangement as claimed in one of claims 10, wherein there is a clearance in one of the heat coupling plates.

15. The arrangement as claimed in claim 12, wherein the further devices are cooling ribs combined with a fan.

16. The arrangement as claimed in claim 8, wherein the small-volume bodies of material with high relative permeability are incorporated in heating/cooling plates on both sides of the sample chamber.

* * * * *